(12) United States Patent
Mosher

(10) Patent No.: US 11,805,852 B1
(45) Date of Patent: Nov. 7, 2023

(54) COMBINED SHOE AND ORTHOTIC SUPPORT

(71) Applicant: Dave Mosher, Glennrock, WY (US)

(72) Inventor: Dave Mosher, Glennrock, WY (US)

( * ) Notice: Subject to any disclaimer, the term of this patent is extended or adjusted under 35 U.S.C. 154(b) by 23 days.

(21) Appl. No.: 18/112,057

(22) Filed: Feb. 21, 2023

(51) Int. Cl.
*A43B 7/22* (2006.01)
*A61F 5/01* (2006.01)

(52) U.S. Cl.
CPC ............ *A43B 7/223* (2013.01); *A61F 5/0113* (2013.01)

(58) Field of Classification Search
CPC ........... A43C 11/12; A43B 7/22; A43B 7/223; A43B 11/00; A61F 5/0111; A61F 5/0113; A61F 5/0127; A61F 5/0195
See application file for complete search history.

(56) References Cited

U.S. PATENT DOCUMENTS

| | | | | |
|---|---|---|---|---|
| 2,598,217 A * | 5/1952 | Bronson | ............... | A61F 5/0195 36/43 |
| 4,217,706 A * | 8/1980 | Vartanian | ............... | A61F 5/0195 36/110 |
| 4,550,721 A | 11/1985 | Michel | | |
| 5,950,333 A * | 9/1999 | Tsen | ....................... | A43B 5/001 36/97 |
| 7,303,538 B2 * | 12/2007 | Grim | ..................... | A61F 5/0195 602/23 |
| 10,791,796 B1 * | 10/2020 | Baker | .................... | A43B 3/242 |
| 10,945,871 B2 | 3/2021 | Patterson et al. | | |
| 2009/0287128 A1 * | 11/2009 | Ingimundarson | ........ | A61H 3/00 602/27 |
| 2011/0034846 A1 * | 2/2011 | Draper | .................. | A61F 5/0111 602/27 |
| 2019/0223555 A1 * | 7/2019 | Iannuzzi | ............. | A43B 1/0027 |
| 2021/0205109 A1 * | 7/2021 | Whiteside | ............. | A61F 5/0111 |
| 2022/0226138 A1 * | 7/2022 | Urbanowicz | ......... | A61F 5/0113 |
| 2023/0082391 A1 * | 3/2023 | Anderson | ............ | A43C 11/008 36/50.1 |

* cited by examiner

*Primary Examiner* — Patrick J. Lynch
(74) *Attorney, Agent, or Firm* — Sanchelima & Associates, P.A.; Christian Sanchelima; Jesus Sanchelima

(57) ABSTRACT

A combined shoe and orthotic support including a bracing assembly, a closing assembly and a protective assembly. The bracing assembly includes a back side support, a left rigid brace, a right rigid brace, and a tongue that are adapted to surround the user's ankle to provide support against ankle issues such as sprains, fractures or the like. The plurality of straps included in the closing assembly allows the user to adjust the bracing assembly around the ankle with a predetermined adjustment. The front side support and the closing assembly further includes laces and a zipper, wherein the laces allow the present invention to be adjusted around the foot and the zipper allows the front side support to be widely opened, allowing the user's foot to be placed in and out of the shoe with ease.

1 Claim, 4 Drawing Sheets

COMBINED SHOE AND ORTHOTIC SUPPORT

BACKGROUND OF THE INVENTION

1. Field of the Invention

The present invention relates to an orthotic shoe and, more particularly, to a combined shoe and orthotic support having a foot brace included in a high-top shoe with zipper to strengthen the ankle.

2. Description of the Related Art

Several designs for orthotics shoes have been designed in the past. None of them, however, include an adjustable foot brace included in a high-top shoe with zipper, an ankle's support, and a plurality of straps to strengthen the ankle.

Applicant believes that a related reference corresponds to U.S. Pat. No. 4,550,721 issued for foot support. Applicant believes that another related reference corresponds to U.S. Pat. No. 10,945,871 issued for orthotic leg support apparatus. None of these references, however, teach of an orthopedic drop-foot brace and ankle support device having an integrally connected shoe.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a foot brace made of a padding material to be comfortable for the user.

It is another object of this invention to provide an article of footwear to increase support for various foot or ankle issues.

It is still another object of the present invention to eliminate the need to wear a separate brace.

It is yet another object of this invention to provide an ideal footwear for anyone who has clubfoot or similar foot disabilities, individuals recovering from a severe ankle sprain or fracture, athletes, etc.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
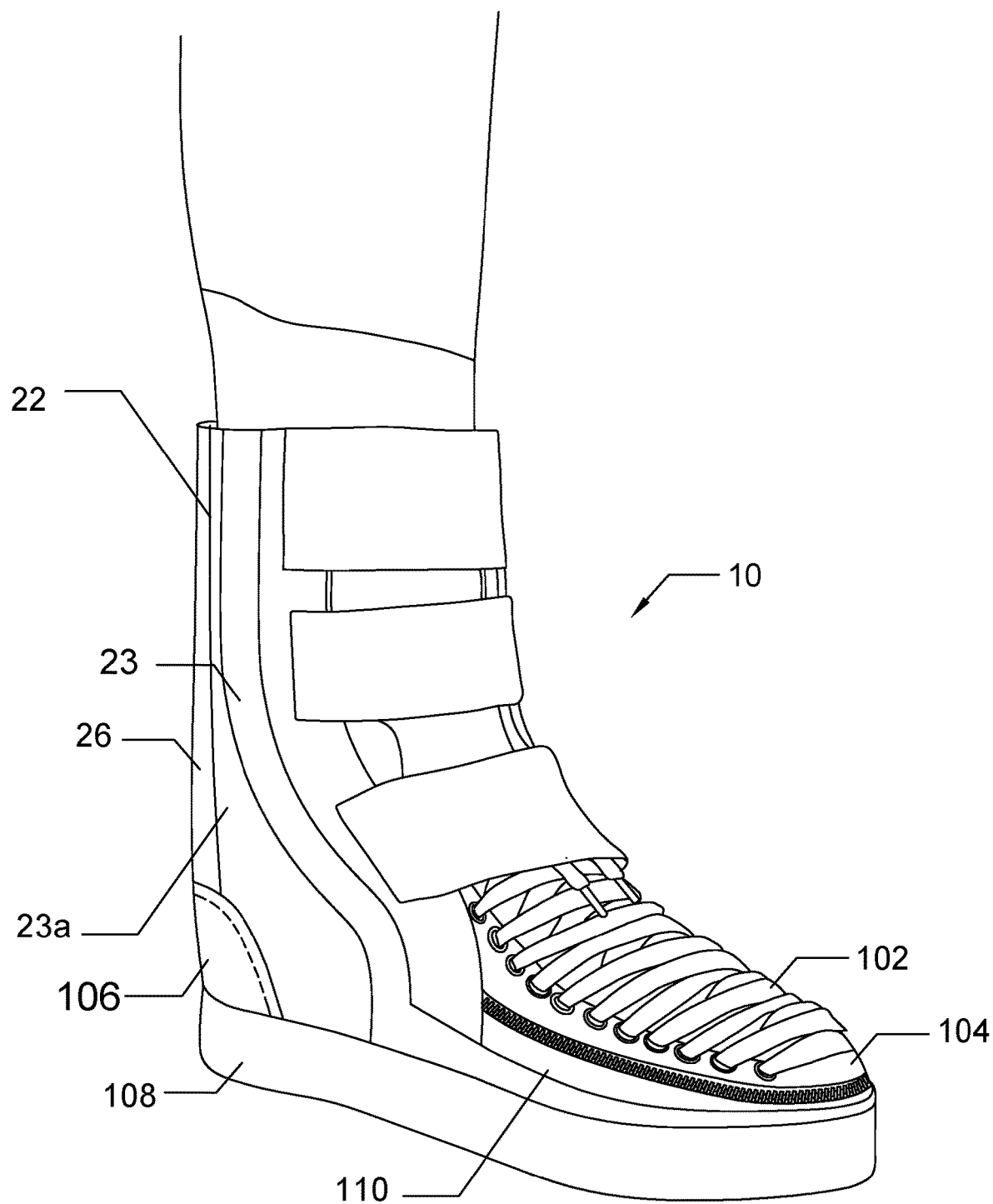
FIG. 1 represents an operational view of an exemplary embodiment of the present invention 10, where a user's foot is adapted to fit into the present invention 10 to enhance support.

Referring now to the drawings, where the present invention is generally referred to with numeral 10, it can be observed that it basically includes bracing assembly 20, a closing assembly 40, a protecting assembly and various exemplary embodiments (100). It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Figure 2:
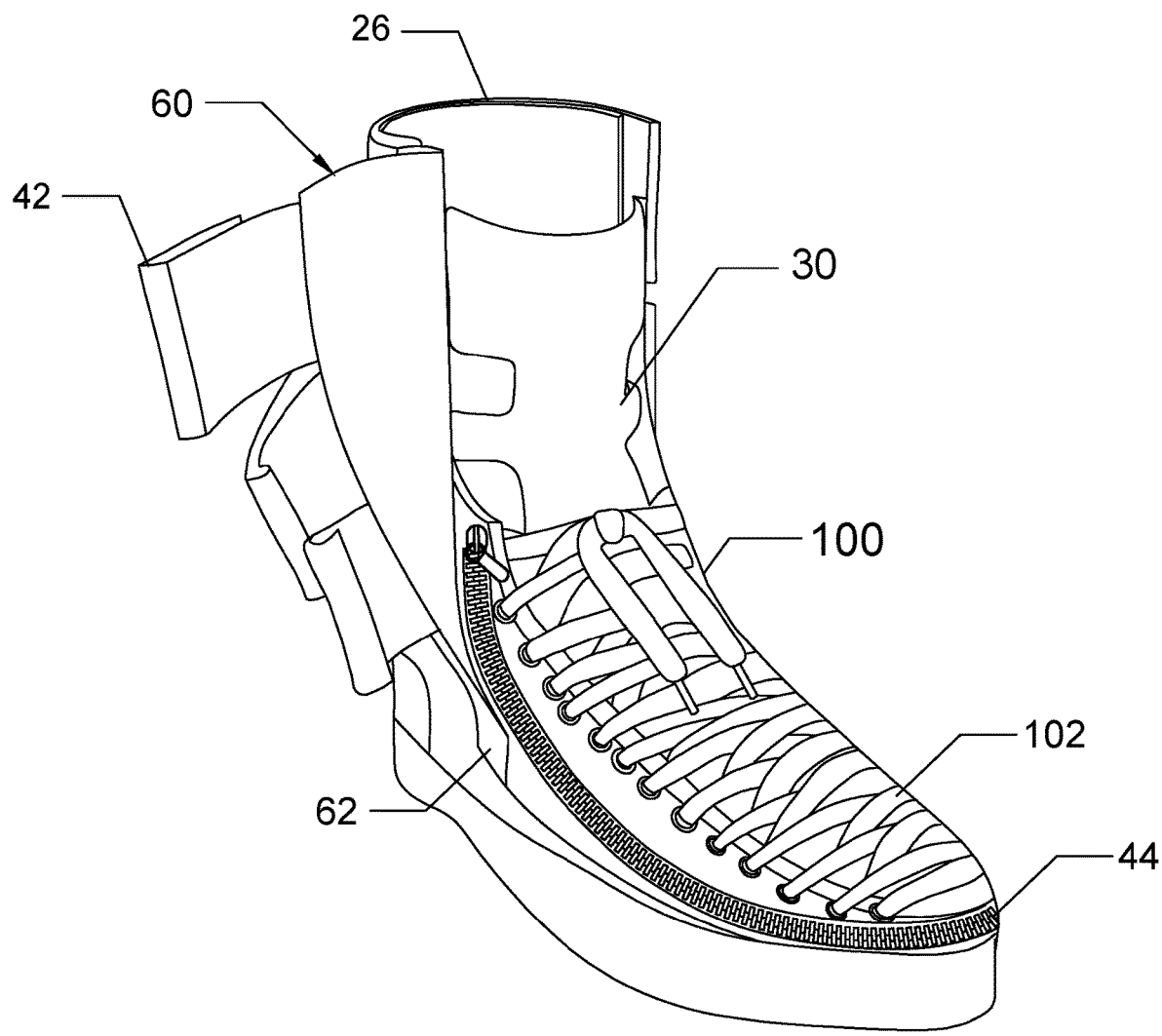
FIG. 2 shows a perspective side view of the present invention 10, wherein the plurality of straps 42 is in an opened configuration and the front side support 28 is in a closed configuration by means of the laces 102 and further secured by a zipper 44.
Figure 3:
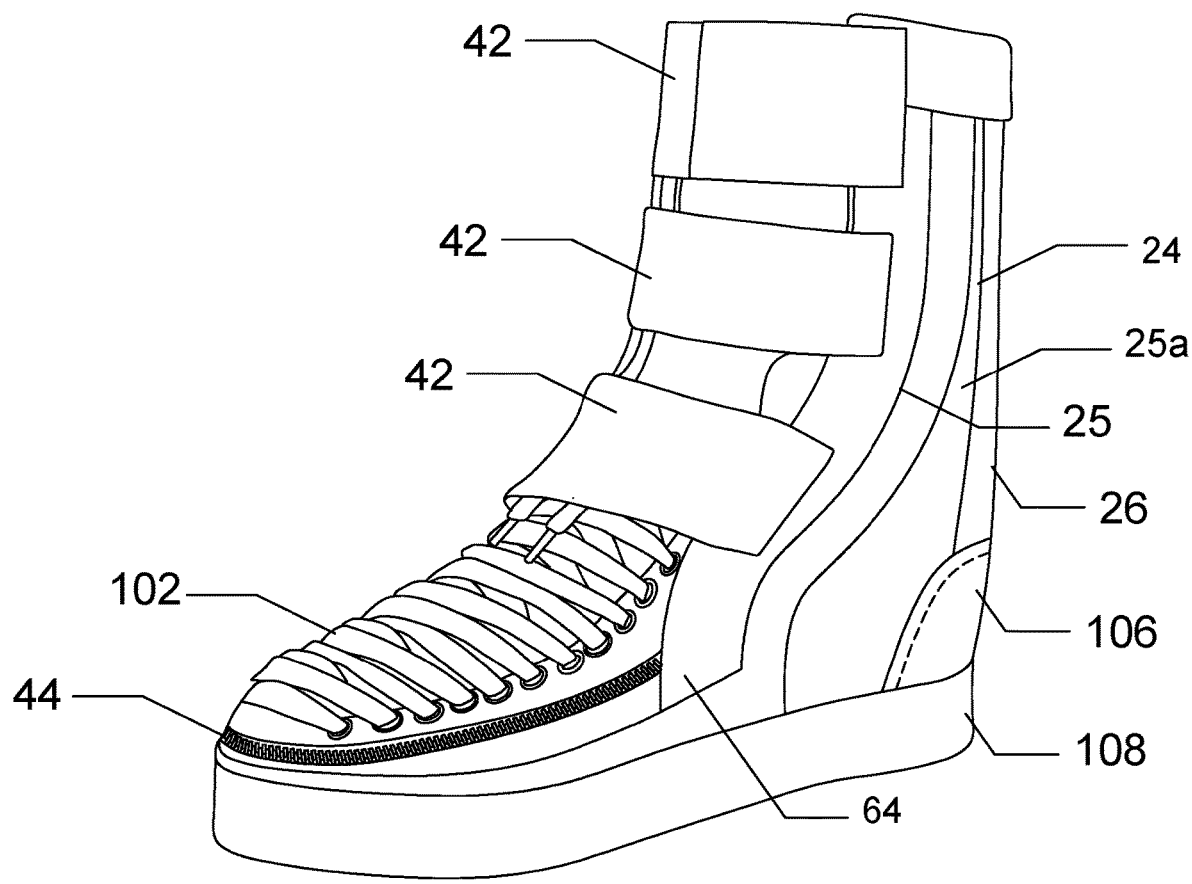
FIG. 3 illustrates an isometric view of a suitable embodiment of the present invention 10, wherein the plurality of straps 42 is attached to the right rigid brace 24, thereby this configuration may provide support to the user's ankle on one or either leg.

Bracing assembly 20 includes a left rigid brace 22, a right rigid brace 24, a back side support 26, and a front side support 28. In an exemplary embodiment, left rigid brace 22 may conform to the left lateral side of the high-top shoe 100, wherein the left rigid brace 22 may extend past the topline thereof. As FIG. 1 illustrates. The left rigid brace 22 may have a suitable height that goes from the sole 108 to a predetermined height to strengthen the user's ankle. In a suitable embodiment, back side support 26 may conform to the back side of the high-top shoe, wherein the back side support 26 may go from the sole 108 to a predetermined height as the left rigid brace 22. As FIG. 1 illustrates. The back side support 26 may be integrally formed with the heel cap 106 bottom portion towards the left rigid brace 22 and the right rigid brace. As FIG. 1 and FIG. 3 depicts. In a preferred embodiment, left rigid brace 22 and right rigid brace 24 may be comprised of brace sections (23, 25) with central portions (23a, 25a), wherein the brace sections (23, 25) may be made of a stiff plastic canvas covered and the central portions (23a, 25a) may be made of a rigid and flexible material such as nylon, neoprene or any other suitable material that helps to protect and/or immobilize the user's ankle. In other embodiment, left rigid brace 22 further includes a left protective strip 62 where a plurality of straps 42 is attached along thereof. The left protective strip 62 protrudes from the lateral side of the left rigid brace 22, wherein the left protective strip 62 may go from a bottom portion of the left rigid brace 22 until a predetermined height thereof. As FIG. 1 represents. In a preferred embodiment, a bottom portion of left protective strip 62 may be attached to the upper 110, as FIG. 2 illustrates, providing support to the user's ankle when closed, wherein the rest of the left protective strip 62 may be pliable to access to the zipper 44, as FIG. 2 represents, and may cover the zipper 44 when closed, as FIG. 1 depicts. It should be considered that the left protective strip 62 may be attached to the rigid section of the left rigid brace, thereby forming a lateral support for the user's ankle, wherein the left protective strip 62 may be made of a flexible material and/or a padding material.

Referring to FIG. 3, the right rigid brace 24 may be attached to the heel cap 106 of the back side support 26, wherein the right rigid brace 24 may be formed from the sole 108, conforming the curved shape of the back side support 26 until a predetermined height of the user's ankle, parallel to a top side of the left rigid brace 22 and the back side support 26. It should be considered that the right rigid brace 24 may be made of rigid fabric such nylon, neoprene or any other suitable material that helps to protect and/or immobilize the user's ankle, wherein the right rigid brace includes a right protective strip 64 where a distal end of the plurality of straps 42 are detached and attached from said right protective strip 64. As best illustrated in FIG. 3. In a preferred embodiment, the right protective strip 64 may be attached from a bottom portion of the rigid fabric of the right rigid brace until a top side thereof, wherein the right protective strip 64 may cover a portion the zipper, although the zipper may begin from this section. It should be considered that the right protective strip 64 of the right rigid brace 24 may be made of a pliable and/or padding material.

Figure 4:
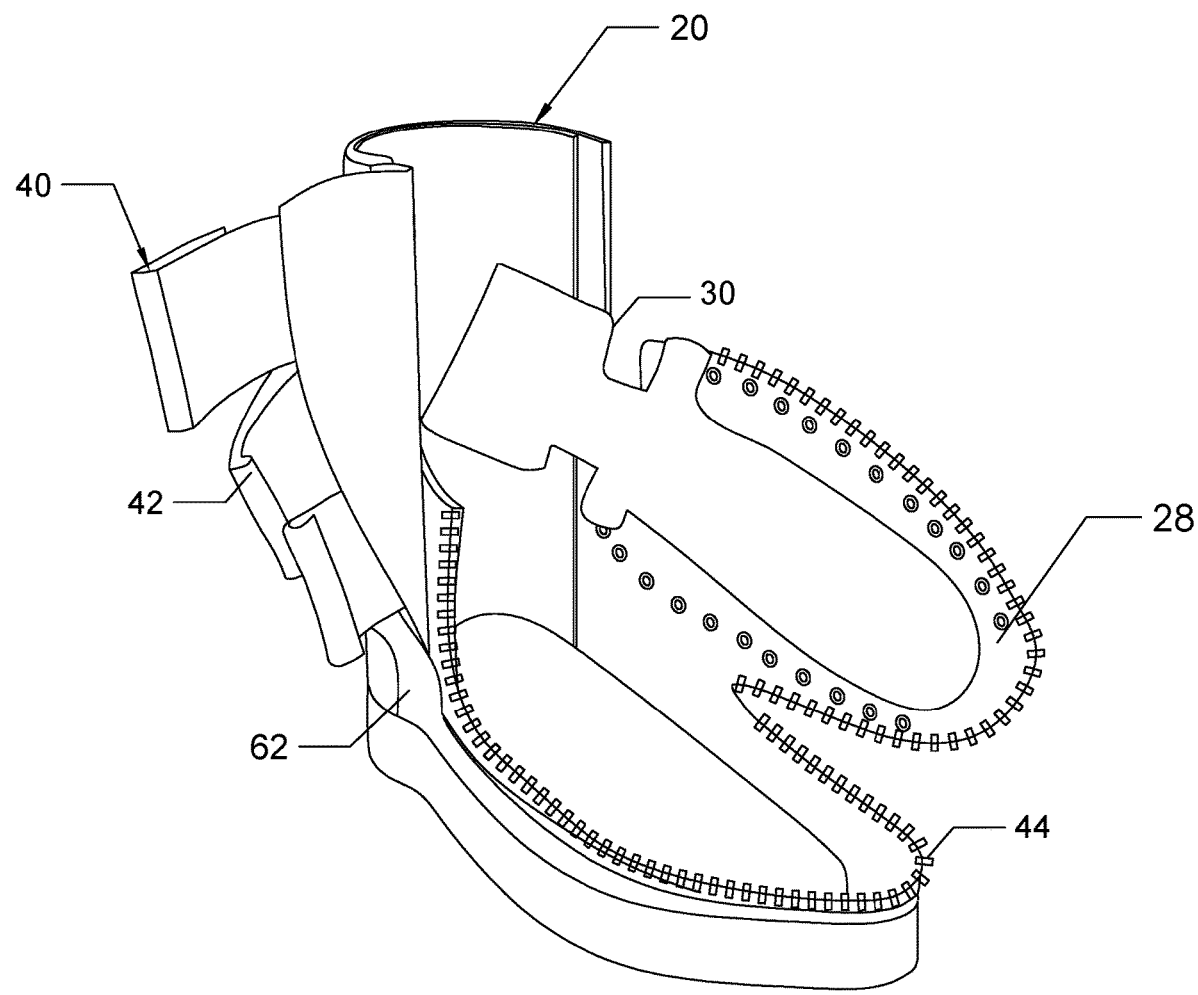
FIG. 4 is a representation of a perspective side view of the present invention 10, wherein the front side support 28 is in an opened configuration by means of unzipping the zipper 44 and detaching the plurality of straps 42, thereby de user interior of the high-top shoe 10 is configured to receive the user's foot without forcing it to enter therein.

Back side support 26 in conjunction with the heel cap 106 may provide support to the back side of the user's ankle, wherein the back side support 26 may be made of a rigid with padding material, wherein the back side support 26 provides support to the left rigid brace 22 and the right rigid brace. In a suitable embodiment, the back side support may be attached to the sole 108 and extends to a predetermined height of the user's ankle. As FIG. 1 demonstrates. In an exemplary embodiment, a portion of the front side support 28 may be attached to the high-top shoe 100 by means of the zipper 44, wherein the front side support 28 includes a tongue 30 and further includes laces 102. As FIG. 2 illustrates. In a suitable embodiment, the front side support 28 may conform with the shape of the user's instep from the topline of the high-top shoe 100 to the toe cap 104 thereof, wherein the front side support 28 may be made of a pliable padded material. In one embodiment, the tongue 30 may be attached to the rear side of the front side support 28, As FIG. 4 illustrates, wherein the tongue 30 may cover the user's instep from the laces 102. It should be considered that the laces 102 may be mounted from the topline of the high-top shoe 100 until the toe cap 104 thereof, providing a means to strengthen the compression to the user's foot. The tongue 30 may be made of a rigid and/or padding material, thereby the tongue 30 may provide protection to the user's foot when the front side support is in a closed configuration. As best depicted in FIG. 2. In a suitable embodiment, the tongue 30 may extend past the top line of the high-top shoe 100 until a proximal top side of the left rigid brace 22 and right rigid brace 24. Nonetheless, it should be considered in a suitable variation thereof that the tongue 30 may extend past the top side of said left rigid brace 22 and right rigid brace 24. In a preferred embodiment, the tongue 30 may have a suitable width to surround a portion of the user's ankle, wherein the plurality of straps 42 may be adapted to secure the tongue against the user's ankle with a predetermined force applied by means of the adjustment between the plurality of straps 42 and the right protective strip 64 of the right rigid brace 24. Thereby the bracing assembly 20 is configured to protect the user's ankle and/or immobilize it when the user may have mobility issues.

Closing assembly 40 includes the plurality of straps 42 and the zipper 44. In an exemplary embodiment, the plurality of straps 42 may be attached to the left protective strip 62 of the left rigid brace 22, as FIG. 1 shows, wherein the plurality of straps are made of an elastic material and/or a flexible material that allows to secure the left rigid brace 22 to the right rigid brace 24 by means of a fastener placed at the distal end of the plurality of straps 42. As FIG. 3 illustrates. The plurality of straps 42 may provide adjustable support to the user's ankle. In a suitable variation thereof, the plurality of straps 42 may have a length that surrounds the bracing assembly 20, thereby the plurality of straps 42 may provide the user's more support and compression if required. In one embodiment, the zipper 44 may be a fastener well known in prior art, wherein the zipper 44 may be placed from the topline of the high-top shoe 100 and proximal to the left rigid brace 22 along the front side support 26 until the bottom side of the right protective strip 64 of the right rigid brace 24 as FIG. 2 and FIG. 3 illustrates. The zipper 44 may allow the front side support to be opened, thereby the user's foot may be placed inside the high-top shoe 100, preventing the user's ankle from being pressed when fitting inside a shoe. As FIG. 4 depicts.

Protective assembly 60 includes the left protective strip 62 and the right protective strip 64. In an exemplary embodiment, the left protective strip 62 and the right protective strip 64 may be extended portions of the left rigid brace 22 and the right rigid brace 24. As FIG. 1 and FIG. 3 represents.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A combined shoe and orthotic support, consisting of:
a bracing assembly including a left rigid brace, a right rigid brace, a back side support, front side support, and a tongue, wherein a combination between a sole, said left rigid brace, said right rigid brace, said back side support, said front side support, and said tongue define a high-top shoe, wherein said left rigid brace and said right rigid brace forms laterals or outer bounds of said high-top shoe, wherein each of said left rigid brace and said right rigid brace have a brace section with a central portion, said central portions are made of a rigid fabric said brace sections of said left rigid brace and said right rigid brace are made of a stiff plastic canvas covered material, wherein said back side support forms a back side of said high-top shoe, said back side support includes an internal padded section that is adapted to receive a back side of a user's ankle, wherein said front side support includes the tongue and laces, wherein said laces are mounted along said front side support from a topline of said high-top shoe to a toe cap, wherein said tongue is attached to a rear side of said front side support covering said laces, wherein said tongue is made of a padded material, wherein said tongue is adapted to be placed on a user's instep and said user's ankle;
a closing assembly having a plurality of straps and a zipper, wherein each strap of said plurality of straps have a rectangular shape, wherein a portion of said plurality of straps is attached to the left rigid brace and another portion thereof is removably attachable to a portion of a right protective strip which surrounds said front side support, said zipper is placed around said front side support from said topline to a bottom side of said right rigid brace, wherein said plurality of straps are made of an elastic material, said elastic material is configured to compress said left rigid brace, said right rigid brace and said back side support against said user's ankle to provide support; and
a protecting assembly including a left protective strip and said right protective strip, wherein said left protective strip, and said right protective strip are strips attached to a lateral edge of said left rigid brace and said right rigid brace respectively, wherein said left protective strip and said right protective strip are adapted to cover a portion of said zipper, wherein a portion of said left protective strip and said right protective strip are attached to a lateral portion of said left rigid brace and said right rigid brace respectively, wherein said left protective strip and said right protective strip are strips made of a padded and flexible material, wherein a bottom portion of said left protective strip is fixed to said high-top shoe to enhance support when said plurality of straps are attached to said right protective strip.

* * * * *